(12) United States Patent
Hoffman

(10) Patent No.: US 7,145,151 B2
(45) Date of Patent: Dec. 5, 2006

(54) REDUCED COMPLEXITY INTERCONNECT FOR TWO DIMENSIONAL MULTISLICE DETECTORS

(75) Inventor: David M. Hoffman, New Berlin, WI (US)

(73) Assignee: GE Medical Systems Global Technology Company, Inc., Waukesha, WI (US)

( * ) Notice: Subject to any disclaimer, the term of this patent is extended or adjusted under 35 U.S.C. 154(b) by 436 days.

(21) Appl. No.: 10/136,088

(22) Filed: May 1, 2002

(65) Prior Publication Data

US 2002/0122127 A1    Sep. 5, 2002

Related U.S. Application Data

(63) Continuation-in-part of application No. 09/751,891, filed on Dec. 29, 2000.

(51) Int. Cl.
*G01T 1/20* (2006.01)
*G01T 1/24* (2006.01)

(52) U.S. Cl. .......................... 250/370.11; 250/370.01; 250/336.1

(58) Field of Classification Search ........... 250/370.11, 250/370.01, 336.1
See application file for complete search history.

(56) References Cited

U.S. PATENT DOCUMENTS

| | | | |
|---|---|---|---|
| 4,195,361 A | | 3/1980 | Hillery |
| 4,219,834 A | | 8/1980 | Esch et al. |
| 4,227,209 A | | 10/1980 | Warner |
| 4,240,845 A | | 12/1980 | Esch et al. |
| 5,107,122 A | * | 4/1992 | Barkan et al. .......... 250/370.01 |
| 5,151,588 A | * | 9/1992 | Kiri et al. ................ 250/208.1 |
| 5,262,649 A | * | 11/1993 | Antonuk et al. ....... 250/370.09 |
| 5,477,214 A | | 12/1995 | Bartel |
| 5,520,178 A | | 5/1996 | Dahn et al. |
| 5,531,714 A | | 7/1996 | Dahn et al. |
| 6,198,800 B1 | * | 3/2001 | Garland et al. ............ 378/98.7 |
| 6,396,898 B1 | * | 5/2002 | Saito et al. ................... 378/19 |

* cited by examiner

*Primary Examiner*—David Porta
*Assistant Examiner*—Christine Sung
(74) *Attorney, Agent, or Firm*—Carl B. Horton, Esq.; Armstrong Teasdale LLP

(57) ABSTRACT

A CT detector module utilizes a simplified FET that effectively sums detector cells in the X direction, allowing for a doubling of scan slices in the Z direction with the same or a lesser number of DAS channels found in conventional CT detector modules.

26 Claims, 3 Drawing Sheets

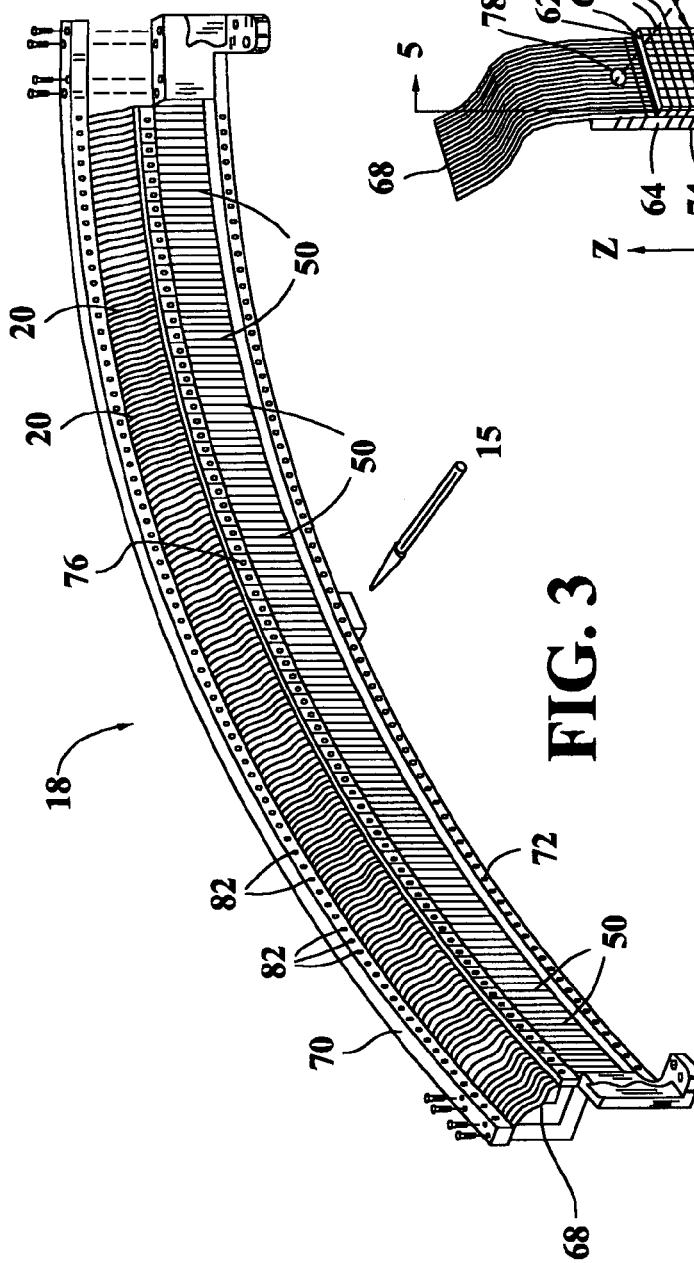
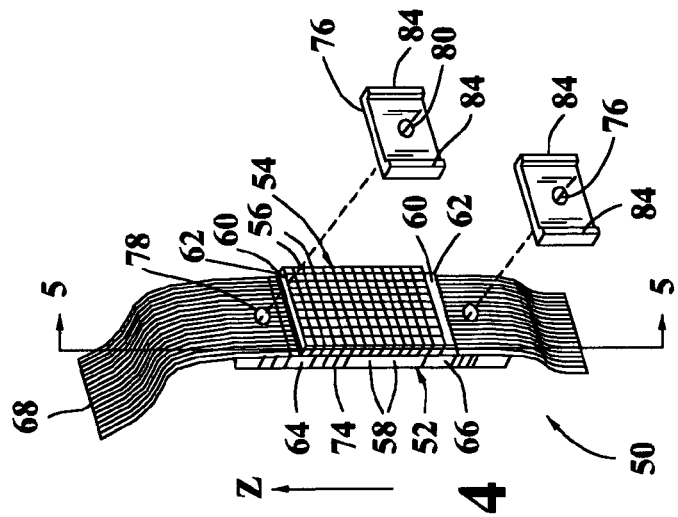
FIG. 3
FIG. 4

REDUCED COMPLEXITY INTERCONNECT FOR TWO DIMENSIONAL MULTISLICE DETECTORS

CROSS REFERENCE TO RELATED APPLICATIONS

This application is a Continuation In Part of U.S. patent application Ser. No. 09/751,891 filed Dec. 29, 2000.

BACKGROUND OF THE INVENTION

This invention relates generally to radiation detectors of the scintillating type, and more particularly to a computer tomograph (CT) detector module having a reduced complexity interconnect and to methods for preparing and using the same.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view." A "scan" of the object comprises a set of views made at different gantry angles, or view angles, during one revolution the x-ray source and detector. In an axial scan, the projection data is processed to construct an image that corresponds to a two dimensional slice taken through the object. One method of reconstructing an image from a set of projection data is referred to in the art as the filtered back projection technique. This process converts the attenuation measurements from a scan into integers called "CT numbers" or "Hounsfield units" which are used to control the brightness of a corresponding pixel in a cathode ray tube display.

At least one known detector CT imaging system includes a plurality of detector modules, each having a scintillator array optically coupled to a semiconductor photodiode array that detects light output by the scintillator array. These known detector module assemblies require an increasing number of scintillator/diode rows in the Z direction, along with associated electronics to support a desire for increasing the number of CT slices of information gathered per CT rotation.

Accordingly, it would be desirable to provide an improved CT detector module design which effectively sums detector cells in the X direction, while allowing for a doubling of scan slices in the Z direction, with the same or lesser number of DAS channels found in a conventional CT detector module.

BRIEF SUMMARY OF THE INVENTION

There is therefore provided, in one embodiment of the invention, an enhanced CT detector module utilizing a simplified FET that effectively sums detector cells in the X direction, allowing for a doubling of scan slices in the Z direction with the same or a lesser number of DAS channels found in conventional CT detector modules.

This incorporates a simpler FET/decoder chip than would be required for a module with an increased number of detector rows in the Z direction or for a module with an option to electrically combine cells in the X direction while increasing detector rows sampled in the Z direction. Fewer FETs are provided although the same number as conventional modules may be used providing a simpler decoder design.

Also, this invention permits summing detector cells in the X direction, which allows a doubling of scan slices in the Z direction with the same number of DAS channels but avoids using more FET switches, a more complex decoder and/or more FET decoder horizontal lines (X-direction) than products designed to accomplish this electronically would use. This invention also reduces overall FET/decoder size and cost, and improves reliability over modules designed to accomplish this electronically.

In addition, this and other embodiments of the invention provide for including a simplified concept wherein some cells float (i.e. they are left open) and their collected charge will re-distribute itself among the neighboring cells. This embodiment allows cell summing in the X direction with a much simpler interconnect scheme (i.e., far fewer FET switches and a simplified decoder). In one embodiment, there is no increase in the number of FET switches/detector pixel to accomplish a doubling of the scan slices.

BRIEF DESCRIPTION OF THE DRAWINGS

FIG. 3 is a perspective view of one embodiment of a CT system detector array of the present invention.

FIG. 4 is a perspective view of one of the detector module assemblies of the detector array shown in FIG. 3.

DETAILED DESCRIPTION OF THE INVENTION

Figure 1:
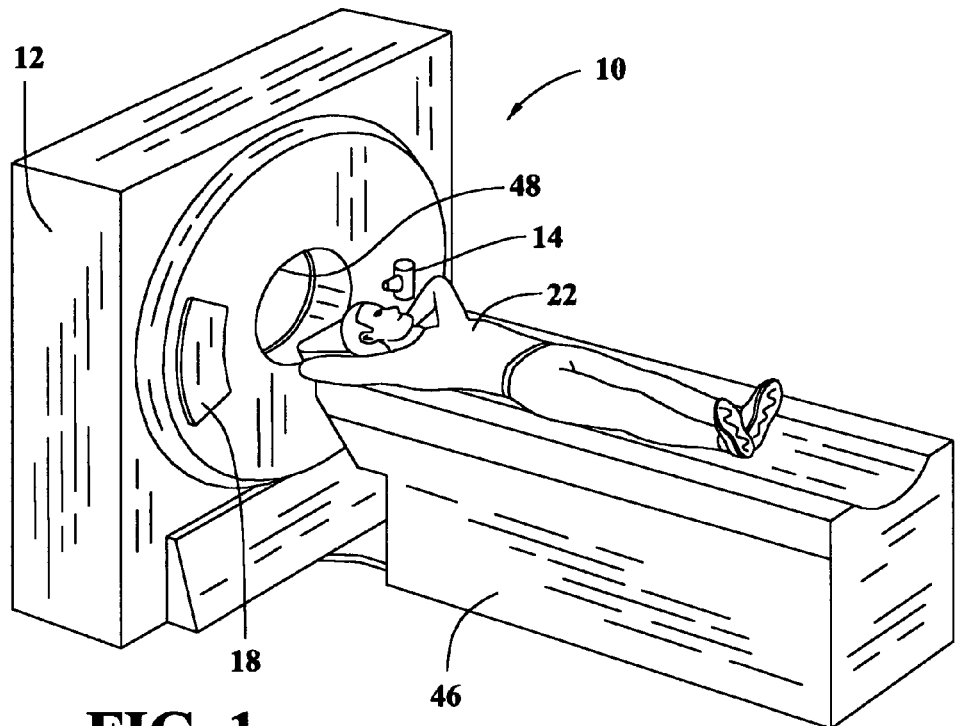
FIG. 1 is a pictorial view of a CT imaging system.
Figure 2:
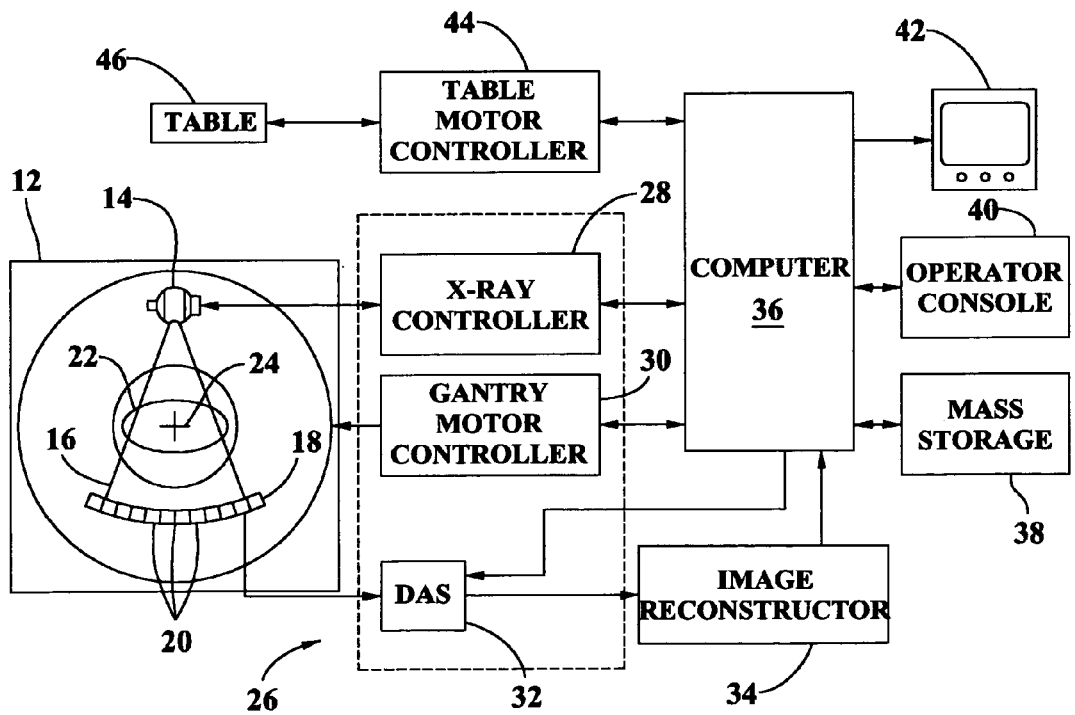
FIG. 2 is a block schematic of the system illustrated in FIG. 1.

Referring to FIG. 1 and FIG. 2, a computed tomography (CT) imaging system 10 is shown as including a gantry 12 representative of a third generation CT scanner. Gantry 12 has an x-ray source that 14 that projects a beam of x-rays 16 toward a detector array 18 on opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 may be fabricated in a single slice or multi-slice configuration. In a multi-slice configuration, detector array 18 has a plurality of rows of detector elements 20, only one of which is shown in FIG. 2.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled a digitized x-ray data from DAS 32 and performs high speed image reconstruction. The reconstructed image is applied as an input to a computer 36 which stores the image in a storage device 38.

Computer 36 also receives commands and scanning parameters from an operator via console 40 that has an input device such as a keyboard and a mouse. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

As shown in FIGS. 3 and 4, detector array 18 includes a plurality of detector module assemblies 50 (also referred to as detector modules), each module comprising an array of detector elements 20. Each detector module 50 includes a high-density photosensor array 52 and a multidimensional scintillator array 54 positioned above and adjacent to photosensor array 52. Particularly, scintillator array 54 includes a plurality of scintillator elements 56, while photosensor array 52 includes photodiodes 58, a switch apparatus 60, and a decoder 62. A material such as a titanium dioxide—filled epoxy fills the small spaces between scintillator elements. Photodiodes 58 are individual photodiodes. In another embodiment, photodiodes 58 are deposited or formed on a substrate. Scintillator array 54, as known in the art, is positioned over or adjacent photodiodes 58. Photodiodes 58 are optically coupled to scintillator array 54 and have electrical output lines for transmitting signals representative of the light output by scintillator array 54. Each photodiode 58 produces a separate low level analog output signal that is a measurement of beam attenuation for a specific scintillator of scintillator array 54. Photodiode output lines (not shown in FIG. 3 or 4) may, for example, be physically located on one side of module 20 or on a plurality of sides of module 20. In the embodiment illustrated in FIG. 4, photodiode outputs are located at opposing sides of the photodiode array.

In one embodiment, and as shown in FIG. 3, detector array 18 includes fifty-seven detector modules 50. Each detector module 50 includes a photosensor array 52 and scintillator array 54, each having a detector element 20 array size of 16×16. As a result, array 18 is segmented into 16 rows and 912 columns (16×57 modules) allowing up to N=16 simultaneous slices of data to be collected along a z-axis with each rotation of gantry 12, where the z-axis is an axis of rotation of the gantry.

Switch apparatus 60 is a multidimensional semiconductor switch array. Switch apparatus 60 is coupled between photosensor array 52 and DAS 32. Switch apparatus 60, in one embodiment, includes two semiconductor switch arrays 64 and 66. Switch arrays 64 and 66 each include a plurality of field effect transistors (FETS) (not shown) arranged as a multidimensional array. Each FET includes an input electrically connected to one of the respective photodiode output lines, an output, and a control (not shown) arranged as a multidimensional array.

Each FET includes an input electrically connected to one of the respective photodiode output lines, an output, and a control (not shown). FET outputs and controls are connected to lines that are electrically connected to DAS 32 via a flexible electrical cable 68. Particularly about one-half of the photodiode output lines are electrically connected to each FET input line of switch 64 with the other one-half of photodiode output lines electrically connected to FET input lines of switch 66. Flexible electrical cable 68 is thus electrically coupled to photosensor array 52 and is attached, for example, by wire bonding.

Decoder 62 controls the operation of switch apparatus 60 to enable, disable, and/or combine photodiode 58 outputs depending upon a desired number of slices and slice resolution for each slide. Decoder 62 in one embodiment, is a FET controller as known in the art. Decoder 62 includes a plurality of output and control lines coupled to switch apparatus 60 and DAS 32. Particularly, the decoder outputs are electrically coupled to the switch apparatus control lines to enable switch apparatus 60 to transmit the proper data from the switch apparatus inputs to the switch apparatus outputs.

Utilizing decoder 62, specific FET's within switch apparatus 60 are selectively enabled, disabled, or combined so that specific photodiode 58 outputs are electrically connected to CT system DAS 32. Decoder 62 enables switch apparatus 60 so that a selected number of rows of photosensor array 52 are connected to DAS 32, resulting in a selected number of slices of data being electrically connected to DAS 32 for processing.

As shown in FIG. 3, detector modules 50 are formed in a detector array 18 and secured in place by rails 70 and 72. FIG. 3 shows rail 72 secured in place, while rail 70 is positioned to be secured over electrical cable 68, over module substrate 74, and mounting bracket 76. Screws (not shown in FIG. 3 or 4) are then threaded through holes 78 and 80 and into threaded holes 82 of rail 70 to secure modules 50 in place. Flanges 84 of mounting brackets 76 are held in place by compression against rails 70 and 72 (or by bonding, in one embodiment) and prevent detector modules 50 from "rocking". Mounting brackets 76 also clamp flexible cable 68 against substrate 74. In one embodiment, flexible cable 68 is also adhesively bonded to substrate 74. If desired, photosensor array can be adhesively bonded to the substrate. Flexible cable 68 is also electrically and mechanically bonded to photosensor array 52, for example, by wire bonding.

Figure 5:
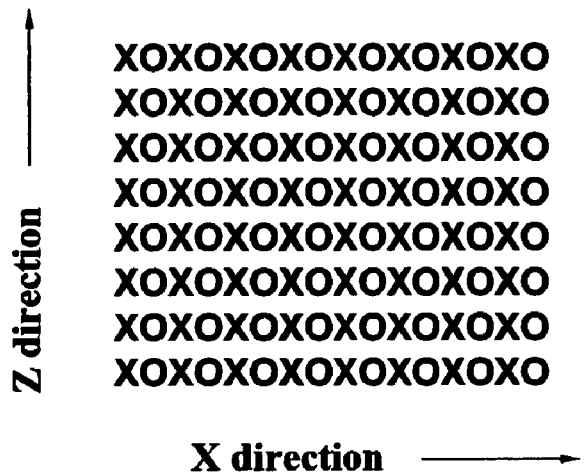
FIG. 5 is a top view of an 8×16 cell array in accordance with one embodiment of the invention.
Figure 6:
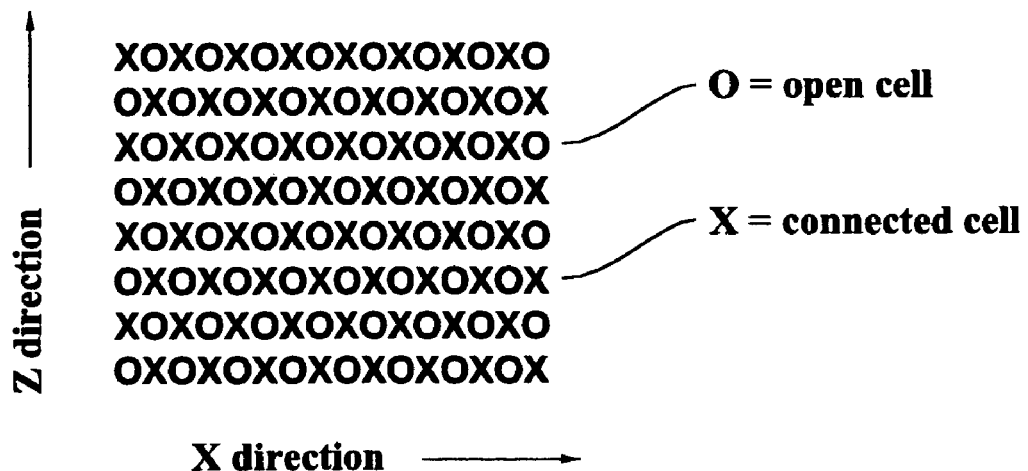
FIG. 6 is a top view of an 8×16 cell array in accordance with another embodiment of the invention.

FIGS. 5 and 6 illustrate alternative embodiments of a photodiode wherein some cells float (i.e. they are left open) and their collected charge automatically re-distributes itself among the adjacent connected cells (only one half of a 16×16 diode array is shown in each of FIG. 5 and FIG. 6). Cells labeled "x" are electrically connected, and cells labeled "o" are those cells that float or are open. This allows cell summing in the X direction with a simpler interconnect scheme than is currently known (i.e. fewer FET switches and a simplified decoder compared to known system improvement designs). In one embodiment there is no increase in the number of FET switches/detector pixel. There is also the capability to increase spatial resolution with the staggered cell design through using interpolation schemes between rows or slices.

In an alternative embodiment, the silicon in the open cell regions allows for a tailoring of the point response or charge collection response. This tailoring is accomplished by modifying the silicon diode sensitivity profile within each diode sensing cell. Such tailoring optionally is selected by a radiologist (or other purchaser) prior to purchase of the CT system to tailor the scan/data collection/sensitivity parameters to the purchaser's desires.

In one embodiment, this concept is used with a finer cell pitch in the X direction than current cell pitches. Also a slice to slice interpolation is performed in one embodiment. In an exemplary embodiment, the slice to slice interpolation is performed with a tailored charge response and/or a tailored open cell silicon design to provide a scheme that is used at all times. This scheme may provide more data slices with fewer DAS channels and/or higher resolution than current designs. This scheme may open the requirements for reflectors, scintillator cell sizes, and other module design parameters.

Referring to FIG. 5, one half of a 16×16 diode array comprising connectable cells, is shown with a Z direction. An X direction is also shown. In this illustrated embodiment of the invention a selected number of cells are combined in the X direction (the number being at least one cell less than the full number of such connectable cells). DAS is thus of constant bandwidth whereby the number of rows that can be processed are doubled.

Referring to FIG. 6, one half of a 16×16 diode array, showing connectable cells, is shown with a Z direction and an X direction. In this illustrated embodiment of the invention, an alternative selected number of cells are combined in the X direction (the number being at least one cell less than the full number of such connectable cells). In an embodiment of this invention, when cells on either side of a center cell are disconnected and only a center cell is connected, the charge on the side cells diffuses and is collected by the center cell. Instead of using FETs to connect cells together, this embodiment uses disconnected cells and allows any charge on a disconnected cell to redistribute itself to cells around the disconnected cells.

Additionally, the design of the photodiode can be modified to change how the charge is distributed. For example, one can tailor cells to redistribute mostly in rows or in columns. Also, the cells in a column is tailor-able to redistribute the charge in all eight adjacent cells, depending upon diffusion in p+ region in cells left unconnected. Typically, current collection in most systems is very crisp so that current cells collect charge in a crisply defined manner, with minimum cross talk to neighboring cells. In this concept rather than minimize cross talk, advantage is taken of it.

One embodiment herein which may be employed to take advantage of the cross talk is to modify the doping of a silicon chip. In this concept, the Si diode cell doping profile is changed whereby the diode structure can be changed. In another modification, a bias can be applied in open pixel to drive the charge.

To preferentially distribute charge, the slopes of P+ doping profile of the diode cell are made asymmetric, the side with the most p+ area, will be the side to which the charge will preferentially migrate in such an embodiment. If there is no change in the diode structure, (i.e. symmetric diode) that results in a symmetric charge redistribution, which is also an acceptable embodiment so it is the easiest way to accomplished results of this invention.

If the p+ regions are moved (i.e. change their locations), a preferential redistribution occurs to cells that are closer to the disconnected regions. The concentration of dopant during the doping of a silicon chip can be changed to give higher concentration in one direction than in another direction, and this moves the charge preferentially. PIN type structure may be employed but embodiments of the invention can use other configurations (e.g. PN structures). The invention is utilized to disconnect some cells and collect the charges from adjacent cells to obtain combinations in x and z directions.

A further method of enhancing the summation of X cells in an embodiment of this invention involves the application of a bias on an open pixel. One may apply a bias voltage to drive charge to adjacent pixels (e.g., to a connected channel corresponding to a middle pixel or to a channel which is connected to a DAS channel). Accordingly, biasing in the either direction can be performed.

In one embodiment, the positive bias can be 0 to 10 volts for a positive bias, e.g. 2 volts, just enough to encourage the migration of charge. This will help to avoid conduction in these regions. This allows flexibility in the number of slices or X resolution with a fixed number of DAS channels.

While the invention has been described in terms of various specific embodiments, those skilled in the art will recognize that the invention can be practiced with modification within the spirit and scope of the claims.

What is claimed is:

1. A method for summing outputs from a diode array in a multislice photodetector, having an array of scintillators optically coupled to an array of diodes, said method comprises summing a number of selectively connected cells in an X direction within the diode array wherein the number of selectively connected cells is less than the total number of cells capable of being connected.

2. A method in accordance with claim 1 wherein the selectively connected cells extend in the X direction.

3. A method in accordance with claim 1 wherein the selectively connected cells extend in a Z direction.

4. A method in accordance with claim 2 wherein each connected cell is adjacent two unconnected cells.

5. A method in accordance with claim 2 wherein the diode cell structure is asymmetric.

6. A method in accordance with claim 2 wherein the diode cell is doped and has a doping profile.

7. A method in accordance with claim 6 wherein the doping profile includes varying dopant concentrations and depths.

8. A method in accordance with claim 7 wherein the varying dopant concentrations and depths are asymmetric.

9. A method in accordance with claim 1 further comprising collecting charge from unconnected calls at adjacent connected cells.

10. A method in accordance with claim 9 wherein said collecting charge comprises obtaining charge concentrations in at least one of the X direction and the Z direction.

11. A method of modifying the charge collection profile in a photodetector system containing a DAS, and comprising an array of scintillators optically coupled to an array of photodiodes, wherein said method comprises selectively coupling cells in the charge regions of the photodiode with the DAS system such that some cells are coupled while other cells are uncoupled.

12. A method in accordance with claim 11 wherein said selectively connected cells are in the X direction.

13. A method in accordance with claim 2 wherein said selectively connected cells extend in the Z direction.

14. A method in accordance with claim 2 wherein said diode is asymmetric.

15. A method of modifying the charge profile in a photodetector system comprising an array of scintillators optically coupled to an array of photodiodes wherein said method comprises optically connecting an asymmetric diode to said array of scintillators.

16. A multislice photodetector, having an array of scintillators optically coupled to an array of diodes, said detector having selectively connected cells in an X direction within the diode array wherein the number of selectively connected cells is less than the total number of cells capable of being connected.

17. A photodetector in accordance with that of claim 16 wherein the selectively connected cells extend in the X direction.

18. A photodetector in accordance with that of claim 16 wherein the selectively connected cells extend in the Z direction.

19. A photodetector in accordance with claim 16 wherein each connected cell is adjacent to two unconnected cells.

20. A photodetector in accordance with claim 16 wherein the diode cell is an asymmetric diode cell.

21. A photodetector in accordance with claim 16 wherein the diode is doped and has a doping profile.

22. A photodetector in accordance with claim 16 wherein the doping profile includes varying dopant concentrations and depths.

23. A photodetector in accordance with claim 16 wherein the varying dopant concentrations and depths are asymmetric.

24. A photodetector in accordance with that of claim 16 wherein charge is collected from unconnected calls at adjacent connected cells.

25. A photodetector in accordance with that of claim 24 wherein said step of collecting charge comprises the step of obtaining charge concentrations in at least one of the X direction and the Z direction.

26. A photodetector in accordance with that of claim 16 wherein a voltage bias is applied to a pixel.

* * * * *

UNITED STATES PATENT AND TRADEMARK OFFICE
CERTIFICATE OF CORRECTION

PATENT NO.         : 7,145,151 B2                                    Page 1 of 1
APPLICATION NO.    : 10/136088
DATED              : December 5, 2006
INVENTOR(S)        : Hoffman It is certified that error appears in the above-identified patent and that said Letters Patent is hereby corrected as shown below:

In Claim 4, column 6, line 38, delete "adjacent two" and insert therefor --adjacent to two--.

In Claim 9, column 6, line 49, delete "unconnected calls" and insert therefor --unconnected cells--.

In Claim 13, column 6, line 63, delete "claim 2 wherein" and insert therefor --claim 12 wherein--.

In Claim 14, column 6, line 65, delete "claim 2 wherein" and insert therefor --claim 12 wherein--.

Signed and Sealed this

First Day of July, 2008

JON W. DUDAS
*Director of the United States Patent and Trademark Office*